United States Patent
Sasaki et al.

(10) Patent No.: US 7,714,289 B2
(45) Date of Patent: May 11, 2010

(54) CHARGED PARTICLE BEAM APPARATUS

(75) Inventors: Yuko Sasaki, Mito (JP); Mitsugu Sato, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 154 days.

(21) Appl. No.: 12/155,347

(22) Filed: Jun. 3, 2008

(65) Prior Publication Data
US 2008/0272300 A1 Nov. 6, 2008

Related U.S. Application Data

(63) Continuation of application No. 10/838,342, filed on May 5, 2004, now Pat. No. 7,425,702.

(30) Foreign Application Priority Data

May 9, 2003 (JP) .............................. 2003-131026

(51) Int. Cl.
G01N 23/00 (2006.01)
(52) U.S. Cl. ........................ 250/311; 250/309; 250/310; 250/396 R
(58) Field of Classification Search ................. 250/306, 250/307, 309, 310, 311, 396 R, 397, 492.1, 250/492.2, 492.3
See application file for complete search history.

(56) References Cited

U.S. PATENT DOCUMENTS

| 4,814,716 | A | | 3/1989 | Kato et al. | |
|---|---|---|---|---|---|
| 6,087,667 | A | * | 7/2000 | Nakasuji et al. | 250/492.2 |
| 6,348,690 | B1 | | 2/2002 | Iwabuchi et al. | |
| 6,437,352 | B1 | * | 8/2002 | Gordon | 250/492.23 |
| 6,452,178 | B2 | | 9/2002 | Iwabuchi et al. | |
| 6,593,152 | B2 | * | 7/2003 | Nakasuji et al. | 438/14 |
| 6,677,585 | B2 | | 1/2004 | Nomura | |
| 7,098,455 | B2 | | 8/2006 | Shinada et al. | |
| 7,227,141 | B2 | * | 6/2007 | Nakasuji et al. | 250/310 |
| 7,247,848 | B2 | * | 7/2007 | Nakasuji et al. | 250/306 |
| 7,425,702 | B2 | * | 9/2008 | Sasaki et al. | 250/310 |
| 2004/0222376 | A1 | * | 11/2004 | Sasaki et al. | 250/310 |
| 2008/0272300 | A1 | * | 11/2008 | Sasaki et al. | 250/310 |
| 2009/0050622 | A1 | * | 2/2009 | Pohl et al. | 219/602 |

(Continued)

FOREIGN PATENT DOCUMENTS

JP 2-291649 A 12/1990

(Continued)

*Primary Examiner*—Bernard E Souw
(74) *Attorney, Agent, or Firm*—McDermott Will & Emery LLP

(57) ABSTRACT

When conditions for an electron gun mainly represented by extraction voltage V1 and accelerating voltage V0 are changed, a charged particle beam is once focused on a fixed position by means of a condenser lens and a virtual cathode position is calculated from a lens excitation of the condenser lens at that time and the mechanical positional relation of the electron gun to set an optical condition. For more accurate setting of the optical condition, a deflecting electrode device is provided at a crossover position of the condenser lens and a voltage is applied to the deflecting electrode device at a constant period so as to control the lens excitation of the condenser lens such that the amount of movement of an image is minimized on an image display unit such as CRT.

6 Claims, 8 Drawing Sheets

U.S. PATENT DOCUMENTS

2009/0101819 A1 * 4/2009 Zhou et al. .................. 250/311

FOREIGN PATENT DOCUMENTS

| JP | 04-190550 | 7/1992 |
| JP | 11-176367 A | 7/1999 |
| JP | 2000-285842 A | 10/2000 |
| JP | 2001-357811 | 12/2001 |
| JP | 2003-016987 | 1/2003 |

* cited by examiner

CHARGED PARTICLE BEAM APPARATUS

RELATED APPLICATIONS

This application is a Continuation of U.S. application Ser. No. 10/838,342, filed May 5, 2004, now U.S. Pat. No. 7,425,702 claiming priority of Japanese Application No. 2003-131026, filed May 9, 2003, the entire contents of each of which are hereby incorporated by reference.

BACKGROUND OF THE INVENTION

The present invention relates to a scanning type charged particle beam apparatus for obtaining a scanning image of a specimen by detecting a signal generated from the specimen by irradiation of a primary charged particle beam.

As well known in the art, in a charged particle beam apparatus having an electron gun comprised of, for example, a cathode, an extraction electrode and an accelerating electrode, when a condition for the electron gun as principally represented by extraction voltage V1 applied across the cathode and the extraction electrode or accelerating voltage V0 applied across the cathode and the accelerating electrode is changed, the position of a virtual cathode changes. This is accounted for by the fact that the intensity of an electric field at the tip of cathode changes to change the trajectory of a charged particle beam emitted from the surface of cathode and besides its trajectory at the extraction electrode, which trajectory coincides with a straight line extending from the virtual cathode existing inside the cathode, is also changed. Therefore, when the extraction voltage V1 and accelerating voltage V0 are made to be variable, an optical condition must be set by taking a change in position of the virtual cathode into consideration. Conventionally, as described in JP-A-11-176367, values of position change amounts calculated in advance through simulation are stored and used for controlling the optical condition.

SUMMARY OF THE INVENTION

In setting the optical condition pursuant to the aforementioned conventional method, it is not particularly checked and confirmed that the optical condition is set correctly. Accordingly, when the optical condition changes owing to, for example, such a change in status of the cathode per se that the radius of curvature of the tip of cathode changes depending on the status of vacuum around the tip, on temperature change and/or on the influence of the electric field, the electric field intensity at the cathode tip changes and the trajectory of the charged particle beam is caused to change, with the result that an actual virtual cathode position deviates from the value calculated through simulation.

In addition, such factors as a mechanical dimensional error between the electrodes and a leakage magnetic field from the outside, particularly, having a component in the same direction as the traveling direction of the charged particle beam also give rise to causes of generation of control errors.

In the past, control errors as above cannot be dealt with. As a result, the position of a focal point (crossover point) of a condenser lens changes and the rotation and magnification of an image changes, thus raising a problem that the condition for observation is changed.

Meanwhile, in scanning the primary charged particle beam, the beam is sometimes blanked during the fly-back interval or period to minimize the amount of charged particle beam irradiated on a specimen. In such a case, a method is employed according to which the crossover point is so set as to a deflected position for blanking, for the purpose of preventing the charged particle beam from being irradiated on an unnecessary portion on the specimen during the fly-back. In the event that the charged particle beam is irradiated unnecessarily excessively on the specimen, unwanted electrification is caused and as the electrified status changes, information obtained from the specimen surface is changed disadvantageously.

In addition, this is also responsible for an increased amount of contamination.

As relevant references, one may also refer to JP-A-2-291649 and JP-A-2000-285842.

As described above, values obtained in advance through simulation have hitherto been used for setting an optical condition in the charged particle beam apparatus.

The present invention contemplates solving the aforementioned problems encountered in the conventional techniques and it is an object of the invention to provide a charged particle beam apparatus which can set a desired optical condition with high reproducibility when conditions for an electron gun, for example, extraction voltage V1 and accelerating voltage V0 are changed and can set an optical condition by taking a change in status around the cathode and mechanical dimensional errors into account.

To accomplish the above object, according to the invention, when an electron gun is comprised of, for example, a cathode, an extraction electrode and an accelerating electrode and such conditions for the electron gun as mainly represented by extraction voltage V1 and accelerating voltage V0 are changed, a charged particle beams is once focused on a fixed position by means of a condenser lens and a virtual cathode position is calculated in accordance with a lens excitation of the condenser lens at that time and the mechanical positional relation of the electron gun to thereby set an optical condition. Further, for the purpose of setting the optical condition more accurately, a deflecting electrode device is provided at a crossover position of the condenser lens and a voltage is applied to the deflecting electrode device at a constant period to move an image measured on an image display unit such as CRT so that the lens excitation of the condenser lens may be controlled in accordance with a minimum one of measured amounts of image movement, thereby ensuring that the optical condition for the primary charged particle beam can always be constant. It is to be noted that the minimum value referred to herein implies a smaller one of a plurality of measured values.

According to the invention, in a charged particle beam apparatus having an electron gun, two or more stages of condenser lens for finely focusing and irradiating a primary charged particle beam emitted from the electron gun on a specimen, deflectors for two-dimensionally scanning the primary charged particle beam on the specimen, signal detectors for detecting signals generated from the specimen by irradiation of the primary charged particle beam, and image display means for displaying a signal from the signal detector as an image, the apparatus comprises voltage controllers for controlling a voltage applied across the cathode of electron gun and the extraction electrode for the primary charged particle beam and a voltage applied across the cathode and the accelerating electrode for accelerating the primary charged particle beam, a condenser lens excitation control unit for controlling the lens excitation of the condenser lens, and means for detecting a difference between a control target value of a crossover position of the primary charged particle beam inside the condenser lens and an actually measured position.

Other objects, features and advantages of the invention will become apparent from the following description of the embodiments of the invention taken in conjunction with the accompanying drawings.

DESCRIPTION OF THE EMBODIMENTS

The present invention will now be described in greater detail by way of example with reference to the accompanying drawings.

Figure 1:
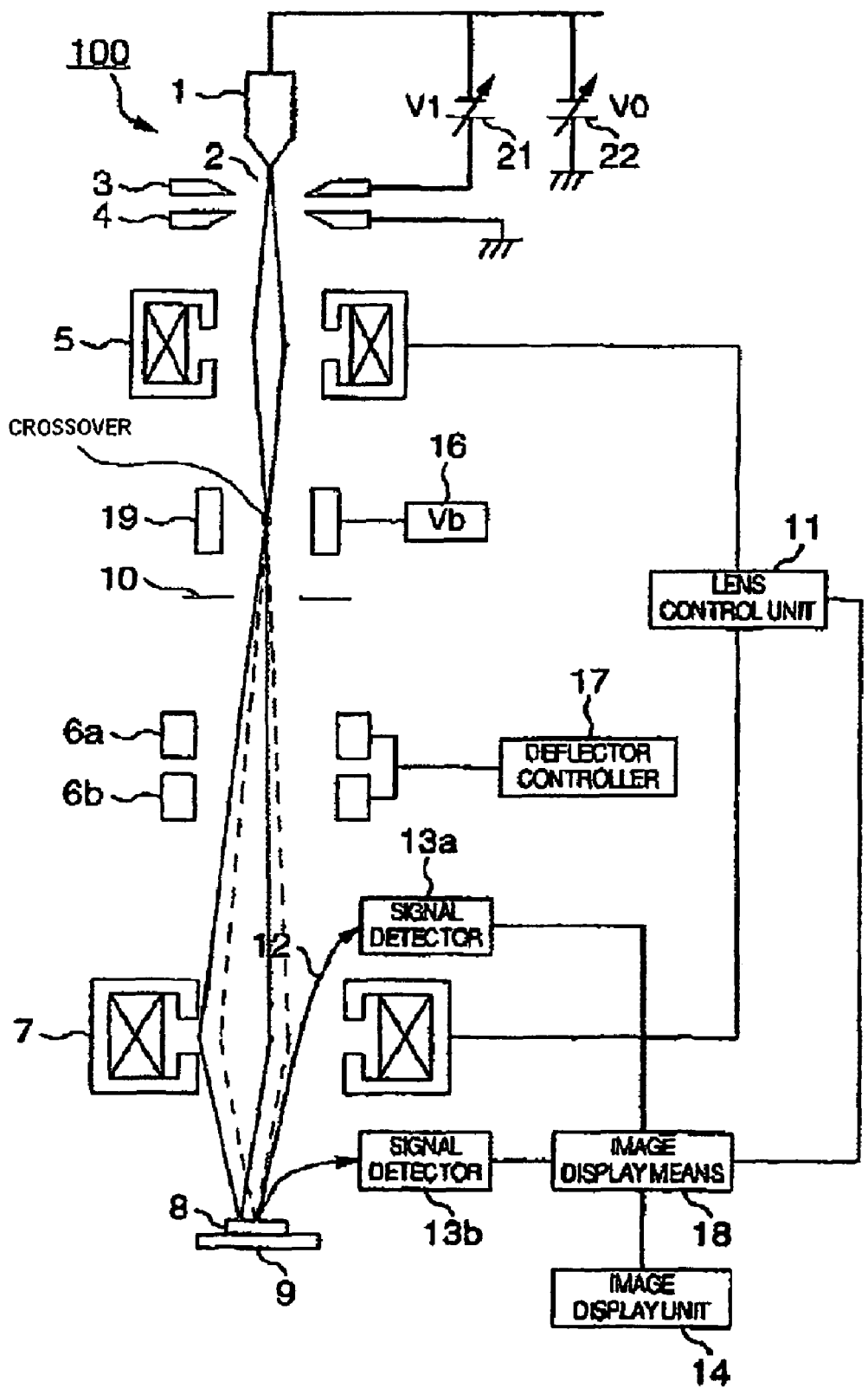
FIG. 1 is a schematic construction diagram of a charged particle beam apparatus according to an embodiment of the invention.

Referring to FIG. 1, a charged particle beam apparatus according to an embodiment of the invention is schematically constructed as shown therein. Generally designated by reference numeral 100 is an electron gun. A primary charged particle beam 2 emitted from a cathode 1 by means of voltage V1 applied across the cathode 1 and an extraction electrode 3 is accelerated by means of accelerating voltage V0 applied across the cathode 1 and an accelerating electrode 4. Voltage controllers 21 and 22 for controlling voltages to be applied as the voltage V1 and accelerating voltage V0 are provided separately or in the form of a unitary means. The primary charged particle beans 2 is removed of an unnecessary region by means of an aperture 10 and is then focused by means of condenser lens 5 and objective lens 7 controlled by a lens control unit 11, that is, a condenser lens excitation control unit so as to be irradiated on a specimen 8. Meanwhile, the beam is scanned two-dimensionally on the specimen 8 by means of deflectors 6a and 6b disposed closer to the cathode 1 than the objective lens 7. The deflectors 6a and 6b are controlled with a deflector controller 17. An information signal 12 generated from the specimen 8 by irradiation of the primary charged particle beam 2 is detected with a signal detector 13a or 13b. The detected signal is passed through an image display means 18 so as to be converted into a brightness modulation signal for an image display unit 14 such as CRT and an enlarged image of the specimen 8 is displayed on the image display unit 14. Though not described, the above constituent components are housed in a vessel in which a vacuum atmosphere suitable for irradiation of the primary charged particle beam is maintained.

When the focal point of the condenser lens 5 always needs to be, for example, at a constant position, a deflecting electrode device 19 is disposed at a corresponding position and voltage Vb is applied to the deflecting electrode device 19 by means of an electrode voltage controller 16. Then, an excitation of the condenser lens is controlled by the lens control unit 11 so that the excitation of the condenser lens 5 can be selected for minimizing the amount of movement of an image on the image display unit 14 and can meet the thus selected minimum (smaller) movement amount.

For controlling the condenser lens 5, a method is available in which the amount of movement of an image is measured by the image display means 18 so that to meet a selected (set) minimum movement amount, the excitation of the condensing lens 5 may be controlled automatically by means of the lens control unit 11.

Figure 2:
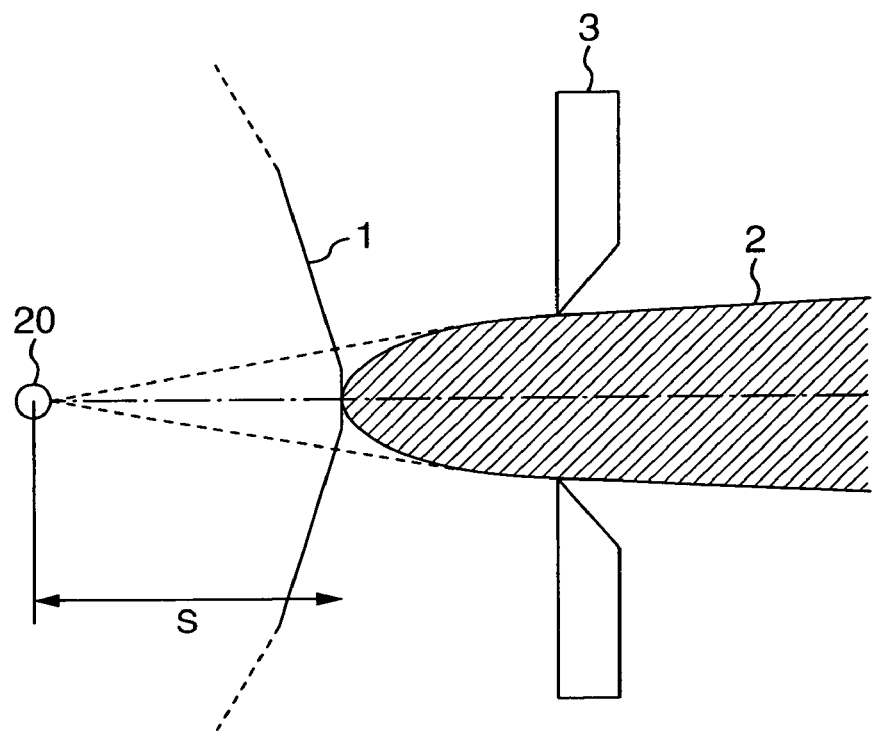
FIG. 2 is a fragmentary sectional diagram useful to explain a virtual cathode position S.

The virtual cathode will be explained by making reference to FIG. 2. As described above, it has been known that in the charged particle beam apparatus having the electron gun comprised of, for example, the cathode, extraction electrode and accelerating electrode, when the condition for the electron gun mainly represented by the extraction voltage V1 applied across the cathode and extraction electrode or the accelerating voltage V0 applied across the cathode and accelerating electrode is changed, the position of the virtual cathode is changed. A charged particle beam is emitted from the tip of cathode 1 along the cathode surface by an electric field of the extraction voltage V1 applied to the extraction electrode 3. At the extraction electrode 3, the trajectory of the charged particle beam coincides with a straight line extending from a virtual cathode 20 existing inside the cathode 1. At that time, the tip of cathode 1 is distant from the virtual cathode by S. In other words, the virtual cathode position is set to S.

Figure 3:
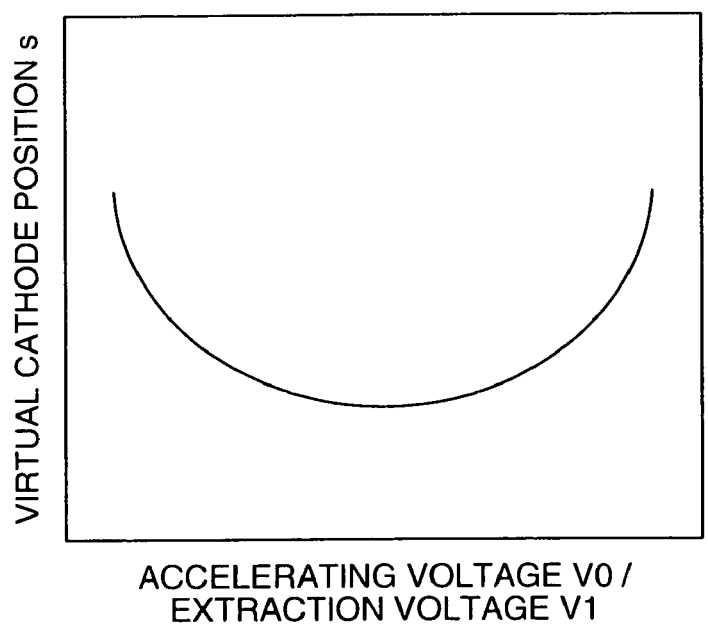
FIG. 3 is a graphic representation showing dependency of the virtual cathode position S upon the ratio of accelerating voltage V0 to extraction voltage V1.

In order to obtain a necessary amount of charged particle beam, it is necessary that the extraction voltage V1 be controlled and besides, the accelerating voltage V0 be controlled in accordance with the kind of specimen and information desired to be obtained. As a result of the control of these voltages, the electric field intensity at the cathode tip changes to change the trajectory of the charged particle beam. Accordingly, the virtual cathode position S is changed. An example of the relation between the ratio of accelerating voltage V0 to extraction voltage V1 and the virtual cathode position S is graphically illustrated in FIG. 3.

Figure 4:
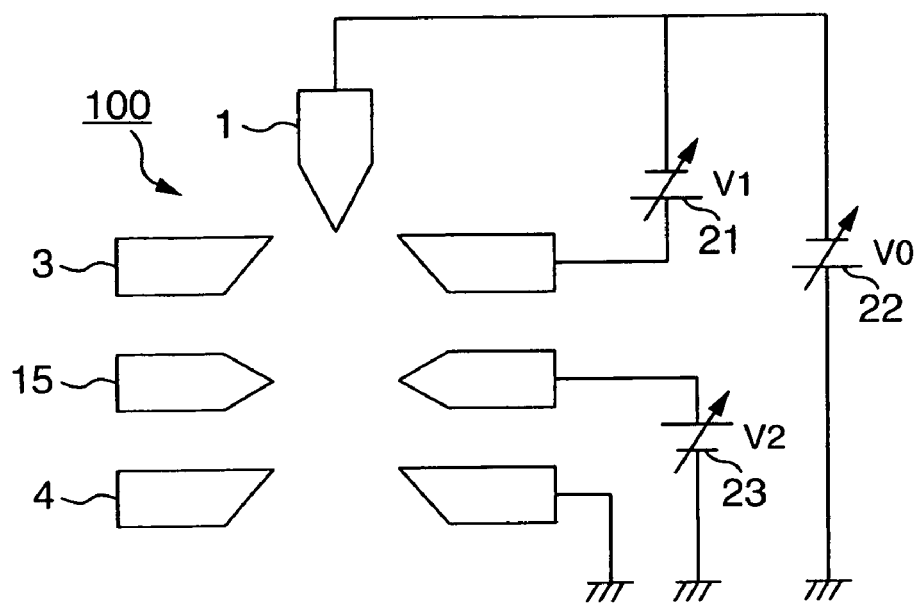
FIG. 4 is a diagram showing the construction of an exemplified electron gun.

The electron gun is exemplarily constructed of cathode 1, extraction electrode 3, control electrode 15 and accelerating electrode 4 as shown in FIG. 4. With this construction, in addition to the constituent components set forth so far, the control electrode 15 is provided and control voltage V2 is applied across the accelerating electrode 4 and the control electrode 15. The control voltage V2 is controlled with a voltage controller 23. It has also been known that when the control voltage V2 is changed, the virtual cathode position S is also caused to change. Graphically illustrated in FIG. 5 is an example of dependency of virtual cathode position S upon the extraction voltage V1 when the control voltage V2 changes to take values indicated by V2(1), V2(2) and V2(3), where these values are related to each other by V2(1)<V2(2)<V2(3).

Figure 5:
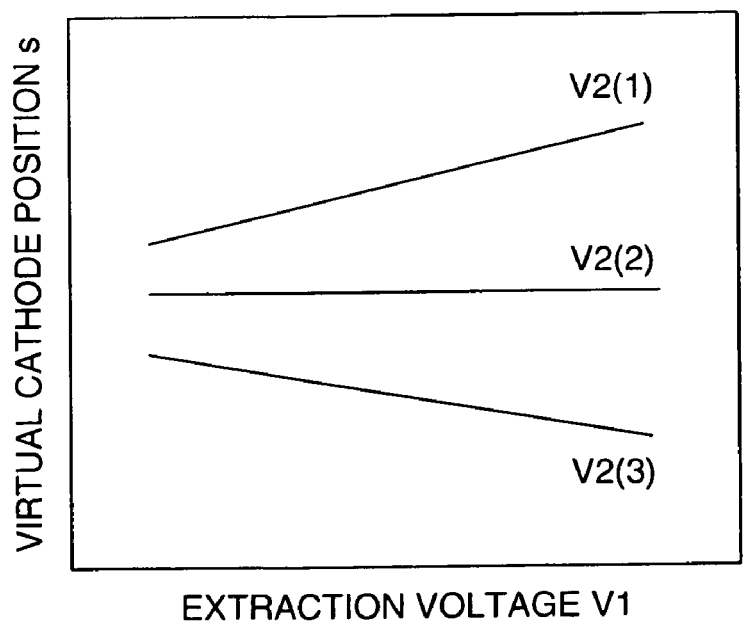
FIG. 5 is a graphic representation showing dependency of the virtual cathode position S upon the extraction voltage V1.

As will be seen from FIG. 5, the virtual cathode position S changes depending upon the shape and distance of cathode 1, extraction electrode 3, control electrode 15 and accelerating electrode 4 as well as the applied voltages.

The lens excitation of condenser lens 5 can be calculated from its lens characteristics if an object point (charged particle emitting point) and an image point (focal point, that is, focal status) are known. In other words, the object point can be calculated if the lens excitation and image point are known. Accordingly, while detecting a focal status by means of the image display means 18, the lens excitation of the condenser lens 5 is controlled such that the beam is once focused on, for example, the aperture 10 by means of the condenser lens 5 disposed closer to the electron gun than the objective lens 7. With the lens excitation of condensing lens 5 for focusing the beam on the aperture 10 known, the object point (in this case, the virtual cathode position) can be calculated from the mechanical positional relation between condenser lens 5 and aperture 10. If the virtual cathode position can be calculated accurately, the focal point (crossover point) of the condenser lens 5 can be controlled on the basis of the lens characteristics of the condenser lens 5.

Figure 6:
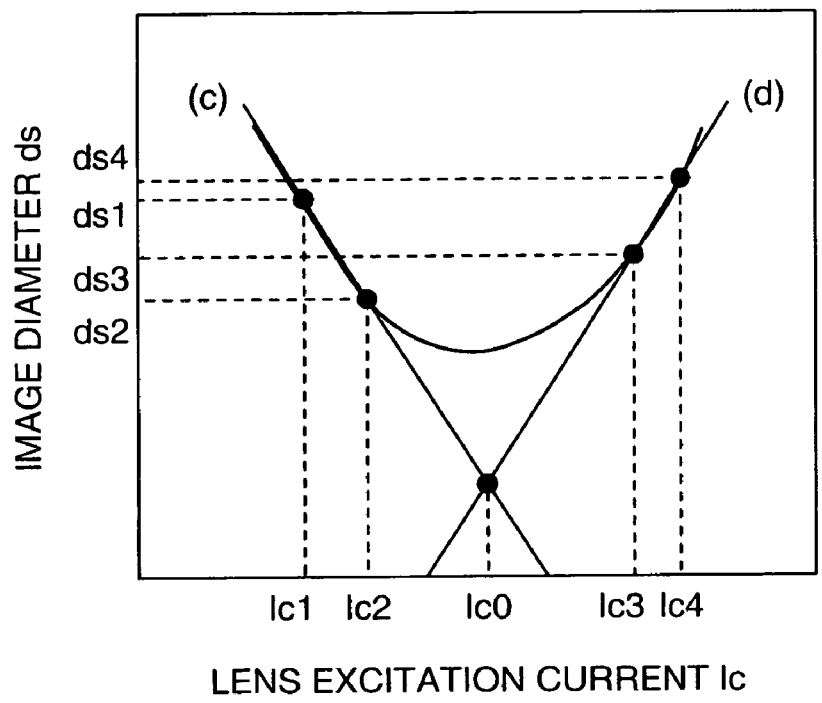
FIG. 6 is a graph showing the relation between lens excitation current of a condenser lens and diameter of an aperture image.

In a method for detecting the focal status on the aperture 10, the size, for example, the diameter of an image of aperture 10 is detected by means of the image display means 18, for instance. The relation between lens excitation current Ic of the condenser lens 5 and diameter ds of the image is illustrated in FIG. 6. The lens excitation Ic of condenser lens 5 is changed through plural points to take values Ic1 to Ic4 and at that time, the diameter ds of the image takes corresponding values ds1 to ds4. Assumptively, the diameter ds of the image traces a quadratic curve. Then, a straight line (c) connecting points (Ic1, ds1) and (Ic2, ds2) and a straight line (d) connecting points (Ic3, ds3) and (Ic4, ds4) are calculated and an intersection of these lines is determined to provide a value of Ic at the intersection which in turn is set as a minimum value Ic0.

Figure 7:
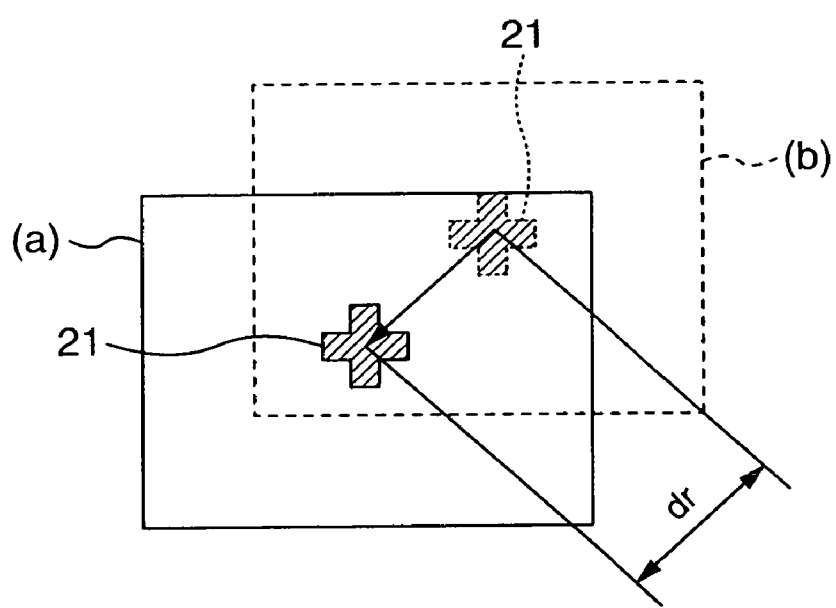
FIG. 7 is a diagram for explaining measurement of an amount of movement of the image.

Movement of the image on the image display unit 14 is illustrated in FIG. 7. For example, a target object 21 is set in the center of the scanning area, that is, a screen (a) of the image display unit 14. When voltage Vb is applied to the deflecting electrode device 19, the target object is moved to, for example, right above (in the drawing) on the screen as indicated in the center of a screen (b). This is because with the voltage Vb applied to the deflecting electrode device 19, the position of the image point moves, so that the scanning area on the specimen 8 is deemed as being moved. An amount of movement of the image of target object 21 on the screen at that time is indicated by dr.

Figure 8:
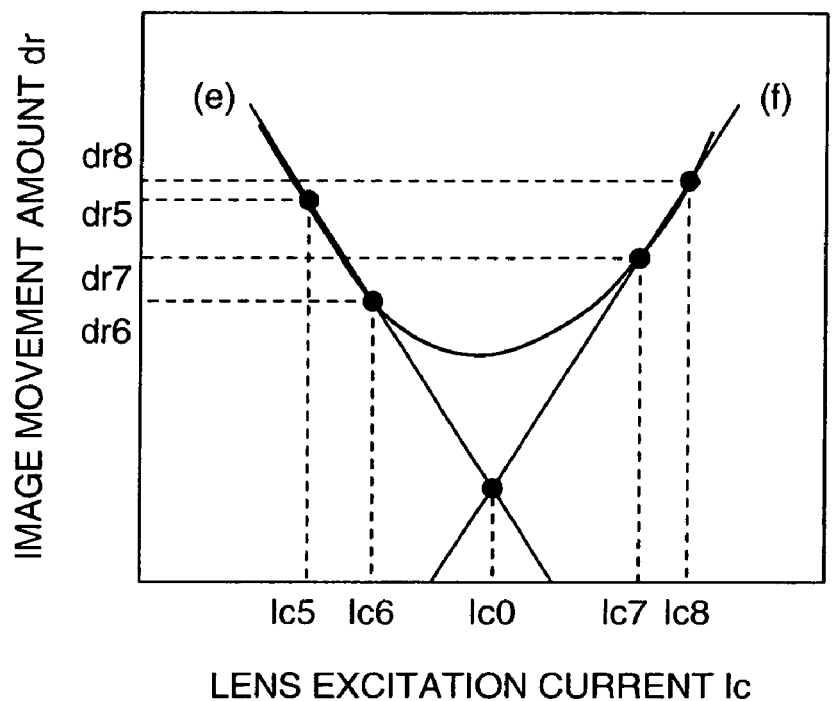
FIG. 8 is a graph showing the relation between the lens excitation current of condenser lens and the amount of image movement.

For setting a lens excitation of condenser lens 5 which minimizes the movement amount, a method is available in which the lens excitation of condenser lens 5 is changed through plural points to measure amounts of movement of the image and a lens excitation condition for minimization is calculated from changes in movement amount. The relation between lens excitation current Ic of condenser lens 5 and image movement amount dr is illustrated in FIG. 8. When the lens excitation of condenser lens 5 is changed through plural points to take values Ic5 to Ic8, corresponding image movement amounts dr are indicated by dr5 to dr8. Assumptively, the movement amount dr traces a quadratic curve. Then, a straight line (e) connecting points (Ic5, dr5) and (Ic6, dr6) and a straight line (f) connecting points (Ic7, dr7) and (Ic8, dr8) are calculated and an intersection of these lines is determined to provide a value Ic at the intersection which in turn is set as a minimum value Ic0.

Further, when the lens excitation of condenser lens 5 is changed from a value determined through the method for focusing the beam on a fixed position to a value calculated from the virtual cathode position S and set and besides the lens excitation of condenser lens 5 is changed through plural points to calculate an excitation condition for minimizing the image movement, a more accurate optical condition can be set.

For example, even when an optical condition is such that the crossover point is set not only at the position of deflecting electrode device 19 but also at another position, the optical condition can also be set accurately through the aforementioned method.

Preferably, these adjustments may be carried out when a condition for observation is changed. Further, even if the condition remains unchanged, a slight change in condition due to a temporal change can be dealt with by making the aforementioned adjustments periodically and therefore, observation and inspection based on a more accurate optical condition can be assured. Through this, a highly reproducible image can be obtained.

Figure 9:
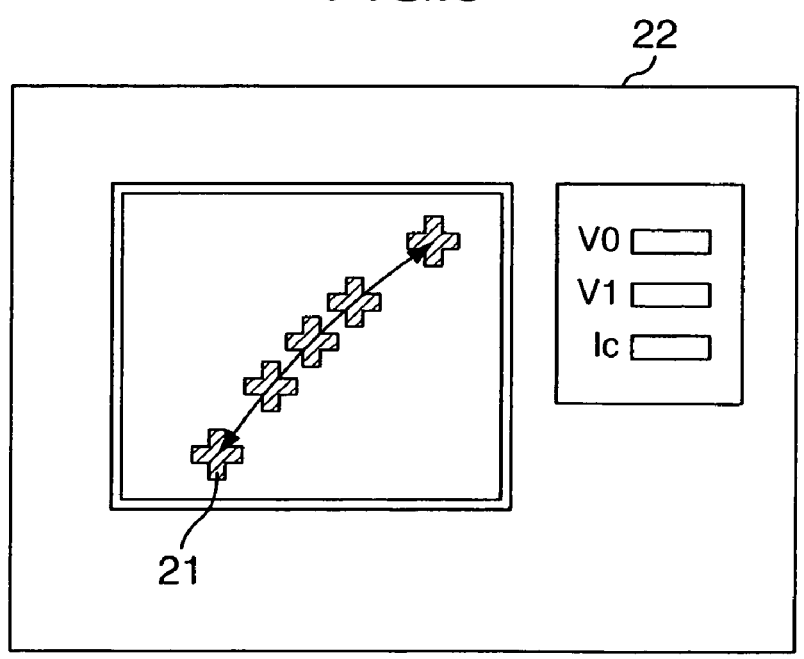
FIG. 9 is a diagram for explaining the display screen.

The procedure for setting the aforementioned crossover point and the condition and adjustment value at that time can be displayed. As shown in a display screen 22 of FIG. 9, the trace of movement of a target object 21, a condition for the electron gun at that time and a lens excitation condition of condenser lens 5 adapted to adjust the crossover point can be displayed. The lens excitation condition is displayed in terms of current value or digit value.

As described above, in a charged particle beam apparatus having an electron gun 100, two or more stages of condenser lens 5 for finely focusing and irradiating a primary charged particle beam 2 emitted from the electron gun 100 on a specimen 8, deflectors 6a and 6b for two-dimensionally scanning the primary charged particle beam 2 on the specimen 8, signal detectors 13a and 13b for detecting a signal 12 generated from the specimen 8 by irradiation of the primary charged particle beam 2 and image display means 18 for displaying, as images, signals of the signal detectors 13a and 13b, the apparatus comprises voltage controllers 21 and 22 for controlling a voltage applied across a cathode 1 of electron gun 100 and an extraction electrode 3 for the primary charged particle beam 2 and a voltage applied across the cathode 1 and an accelerating electrode 4 for accelerating the primary charged particle beams 2, a condenser lens excitation control unit for controlling the lens excitation of the condenser lens 5, that is, a lens control unit 11 and means for detecting a difference between a control target value of a crossover position of the primary charged particle beam 2 inside the condenser lens 5 and an actually measured position.

In addition, there is provided a charged particle beam apparatus which comprises means for taking the control target position of crossover of the condenser lens 5 as a blanking deflection start point to serve as crossover position detection means so as to control a blanking voltage and detect a movement of an image at the time that the blanking deflection starts.

Further, a charged particle beam apparatus is provided which comprises means for applying a voltage to the deflecting electrode device 19 and controlling the condenser lens 5 such that the amount of movement of an image on an image display unit 14 is minimized.

Further, a charged particle beam apparatus is provided which comprises means for changing the lens excitation of the condenser lens 5 through at least two or more points to measure amounts of movement of an image on the image display unit 14 and calculating a lens excitation condition for minimizing the movement amount.

Furthermore, a charged particle beam apparatus is provided which comprises means for displaying the lens excitation condition.

Furthermore, a charged particle beam apparatus is provided which comprises means for displaying, on the image display unit 14, an image movement picture in the course of calculation of the image movement amount.

Furthermore, a charged particle beam apparatus is provided which comprises a control electrode 15 between the extraction electrode 3 and the accelerating electrode 4 and means for applying to the control electrode 15 a voltage for controlling spread of the primary charged particle beam 2 extracted from the cathode 1 by means of the extraction electrode 3.

Figure 10:
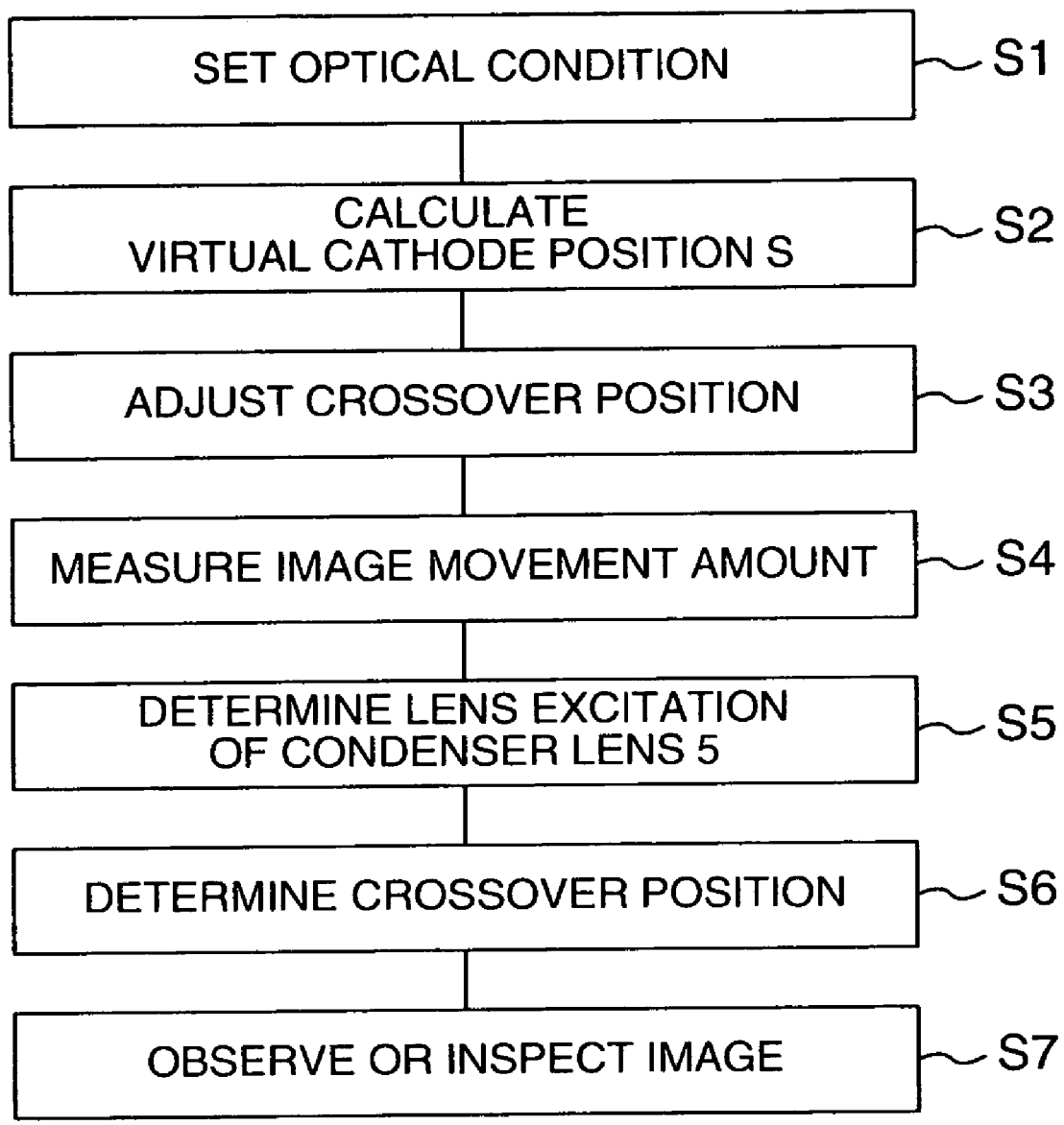
FIG. 10 is a flowchart of an optical condition setting procedure.

Referring now to FIG. 10, there is illustrated a flowchart of an optical condition setting procedure. In the figure, an initial optical condition is first set (S1) and a virtual cathode position S is calculated through the aforementioned method (S2). On the basis of the virtual cathode position, a crossover position is set, that is, the position adjustment is carried out (S3). Because of the nature of the processing apparatus represented by a computer, calculation of the virtual cathode position and that of the crossover position can be carried out substantially simultaneously. An amount of image movement is measured (S4) and a lens excitation of the condenser lens 5 is determined in a manner described as above (S5). The crossover position is determined (S6) and image observation or inspection is carried out (S7).

Figure 11:
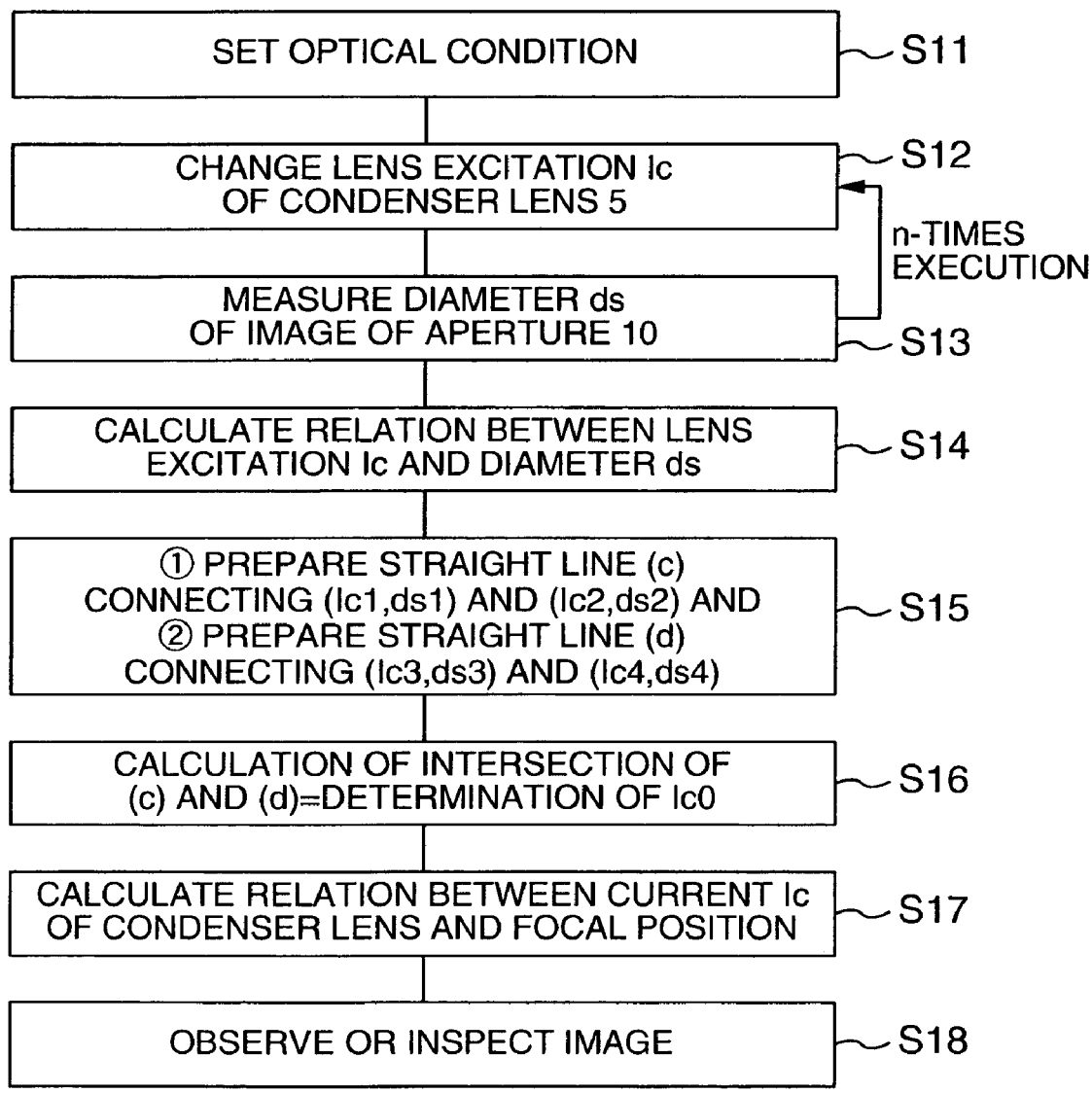
FIG. 11 is a flowchart of an image diameter detection method.

Turning to FIG. 11, there is illustrated a flowchart of an image diameter detection method. In the figure, an initial optical condition is first set (S11), the lens excitation current Ic of condenser lens 5 is changed (S12) and a diameter ds of an image of aperture 10 is measured (S13). These steps are executed n times. The relation between lens excitation current Ic and diameter ds is calculated (S14). ① An expression of straight line (c) connecting points (Ic1, ds1) and (Ic2, ds2) and ② an expression of straight line (d) connecting points (Ic3, ds3) and (Ic4, ds4) are prepared (S15). A value Ic0 is determined through calculation of an intersection of the straight lines (c) and (d) to obtain a control signal (S16). With the Ic0 determined, a virtual cathode position S can be calculated, thereby ensuring that the relation between excitation condition and focal point can be calculated from the lens characteristics of the condenser lens (S17). By setting a desired condition including that for the condenser lens through the above adjustment, an image can be observed under a more accurate condition. The condenser lens 5 is controlled on the basis of the control signal and image observation or inspection is carried out (S18).

Figure 12:
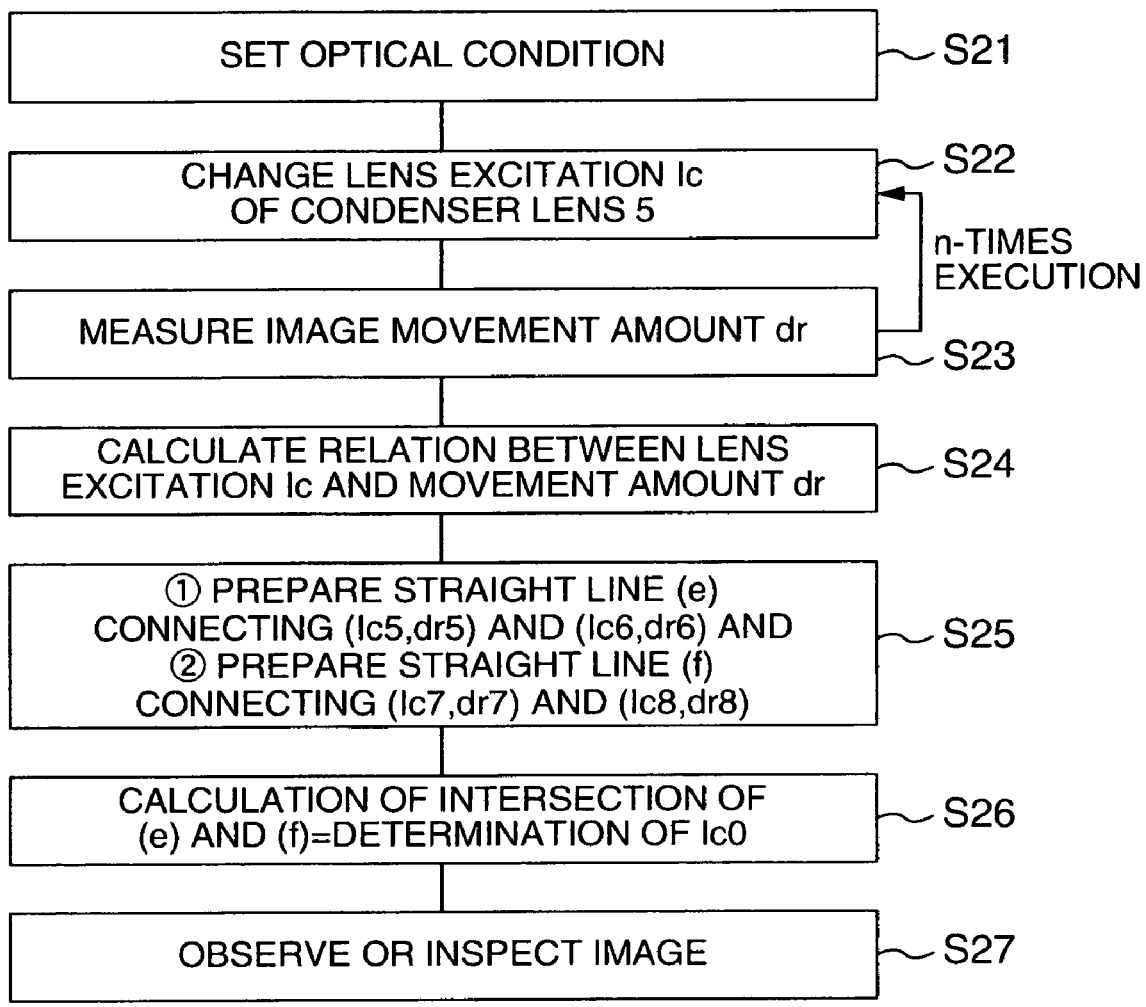
FIG. 12 is a flowchart of an image movement amount detection method.

Referring to FIG. 12, there is illustrated a flowchart of an image movement amount detection method. In the figure, an initial optical condition is first set (S21), the lens excitation current Ic of condenser lens 5 is changed as described previously (S22) and an image movement amount dr is measured (S23). These steps are executed n times and then the relation between lens excitation current Ic and movement amount dr is calculated (S24). ① A straight line (e) connecting points (Ic5, dr5) and (Ic6, dr6) and ② a straight line (f) connecting points (Ic7, dr7) and (Ic8, dr8) are prepared (S25) and an intersection of the lines (e) and (f) is calculated to determine a value Ic0 (S26). By controlling the condenser lens 5 through the use of the Ic0, image observation or inspection is carried out (S27).

According to the present invention, the charged particle beam apparatus can be provided in which when the conditions for the electron gun, for example, extraction voltage V1 and accelerating voltage V0 are changed, a desired optical condition can be set with high reproducibility and besides an optical condition considering a change in status around the cathode and mechanical dimensional errors can be set.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. A charged particle beam apparatus having an electron gun, two or more stages of condenser lens for finely focusing and irradiating a primary charged particle beam emitted from said electron gun on a specimen, deflectors for two-dimensionally scanning said primary charged particle beam on said specimen, signal detectors for detecting a signal generated from said specimen by irradiation of said primary charged particle beam, and an image display unit for displaying, as images, signals of said signal detectors, said apparatus comprising:

voltage controllers for controlling an extraction voltage applied across a cathode of said electron gun and an extraction electrode for the primary charged particle beam and an accelerating voltage applied across said cathode and an accelerating electrode for accelerating said primary charged particle beam;

a condenser lens excitation control unit for controlling the lens excitation of said condenser lens; and a virtual cathode calculation unit for determining focal status on the basis of the lens excitation of said condenser lens selected to minimize the image movement amount on a screen of the image display unit when the lens excitation of the condenser lens is changed through plural points and for calculating a virtual cathode position by using the lens excitation of the condenser lens determined by the focal status;

wherein said condenser lens excitation control unit controls a crossover position of the primary charged particle beam by the virtual cathode position calculated by said virtual cathode calculation unit.

2. A charged particle beam apparatus according to claim 1, wherein said condenser lens excitation control unit controls said condenser lens to minimize the image movement amount on the screen of said image display unit.

3. A charged particle beam apparatus according to claim 1, wherein said virtual cathode calculation unit changes the lens excitation of the condenser lens through at least two points.

4. A charged particle beam apparatus having an electron gun, two or more stages of condenser lens for finely focusing and irradiating a primary charged particle beam emitted from said electron gun on a specimen, deflectors for two-dimensionally scanning said primary charged particle beam on said specimen, signal detectors for detecting a signal generated from said specimen by irradiation of said primary charged particle beam, and an image display unit for displaying, as images, signals of said signal detectors, said apparatus comprising:

voltage controllers for controlling an extraction voltage applied across a cathode of said electron gun and an extraction electrode for the primary charged particle beam and an accelerating voltage applied across said cathode and an accelerating electrode for accelerating said primary charged particle beam;

a condenser lens excitation control unit for controlling the lens excitation of said condenser lens; and a virtual cathode calculation unit for determining focal status on the basis of the lens excitation of said condenser lens selected to minimize a size of an image of an aperture on a screen of the image display unit when the lens excitation of the condenser lens is changed through plural points and for calculating a virtual cathode position by using the lens excitation of the condenser lens determined by the focal status;

wherein said condenser lens excitation control unit controls a crossover position of the primary charged particle beam by the virtual cathode position calculated by said virtual cathode calculation unit.

5. A charged particle beam apparatus according to claim 4, wherein said condenser lens excitation control unit controls said condenser lens to minimize the size of the image of the aperture on the screen of said image display unit.

6. A charged particle beam apparatus according to claim 4, wherein said virtual cathode calculation unit changes the lens excitation of the condenser lens through at least two points.

* * * * *